US009498772B2

(12) United States Patent
Sun et al.

(10) Patent No.: US 9,498,772 B2
(45) Date of Patent: Nov. 22, 2016

(54) UNSUPPORTED METAL SUBSTITUTED HETEROPOLYACID CATALYSTS FOR DIMERIZATION AND/OR OLIGOMERIZATION OF OLEFINS

(71) Applicant: Saudi Arabian Oil Company, Dhahran (SA)

(72) Inventors: Miao Sun, Dhahran (SA); Wei Xu, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 185 days.

(21) Appl. No.: 14/091,137

(22) Filed: Nov. 26, 2013

(65) Prior Publication Data

US 2015/0148578 A1    May 28, 2015

(51) Int. Cl.
| | |
|---|---|
| *C10L 10/10* | (2006.01) |
| *C10L 1/04* | (2006.01) |
| *C07C 2/18* | (2006.01) |
| *C07C 2/14* | (2006.01) |
| *B01J 27/19* | (2006.01) |

(52) U.S. Cl.
CPC .................. *B01J 27/19* (2013.01); *C07C 2/14* (2013.01); *C07C 2/18* (2013.01); *C10L 1/04* (2013.01); *C10L 10/10* (2013.01); *B01J 2523/00* (2013.01); *C07C 2523/04* (2013.01); *C07C 2523/28* (2013.01); *C07C 2527/19* (2013.01); *C10L 2200/043* (2013.01); *C10L 2200/0423* (2013.01); *C10L 2200/0438* (2013.01); *C10L 2200/0446* (2013.01); *C10L 2270/023* (2013.01); *C10L 2270/026* (2013.01); *C10L 2270/04* (2013.01)

(58) Field of Classification Search
CPC .................................................. C07C 2531/14
USPC .................................. 585/512, 513, 508, 510
See application file for complete search history.

(56) References Cited

U.S. PATENT DOCUMENTS

| | | | | |
|---|---|---|---|---|
| 4,375,576 A | * | 3/1983 | Smith, Jr. ................. | C07C 2/28 585/510 |
| 4,398,920 A | | 8/1983 | Guibet et al. | |
| 5,189,201 A | | 2/1993 | Sano et al. | |
| 5,744,678 A | * | 4/1998 | Aida ..................... | B01J 31/143 502/113 |

(Continued)

FOREIGN PATENT DOCUMENTS

| | | |
|---|---|---|
| CA | 2046374 A1 | 1/1992 |
| CN | 85102831 A | 8/1986 |

(Continued)

OTHER PUBLICATIONS

Hauge K et al: "Oligomerization of isobutene over solid acid catalysts", Catalysis Today, Elsevier, NL, vol. 100, No. 3-4, Feb. 28, 2005, pp. 463-466, XP027835042, ISSN: 0920-5861, [retrieved on Feb. 28, 2005].

(Continued)

*Primary Examiner* — In Suk Bullock
*Assistant Examiner* — Aaron Pierpont
(74) *Attorney, Agent, or Firm* — Leason Ellis LLP

(57) ABSTRACT

The present invention relates to unsupported metal (e.g., cesium) substituted heteropolyacid catalyst compositions useful for the production of butene dimers and/or oligomers from a mixed butenes feed, in which, under mild conditions, all isomers of mixed butenes produce highly branched C8 and C8+ olefins.

20 Claims, 1 Drawing Sheet

(56) References Cited

U.S. PATENT DOCUMENTS

| | | | |
|---|---|---|---|
| RE41,341 E | 5/2010 | Atkins et al. | |
| 2007/0213576 A1* | 9/2007 | Brown | C07C 2/12 585/533 |

FOREIGN PATENT DOCUMENTS

| | | |
|---|---|---|
| DE | 197 34 176 | 2/1999 |
| EP | 0 561 284 | 9/1993 |
| EP | 2026904 A1 | 2/2009 |
| GB | 2024812 | 1/1980 |
| JP | 57014538 A | 1/1982 |
| JP | 2005015383 A | 1/2005 |
| JP | 2010260768 A * | 11/2010 |

OTHER PUBLICATIONS

Marchionna M et al: "Light olefins dimerization to high quality gasoline components", Catalysis Today, Elsevier, NL, vol. 65, No. 2-4, Feb. 20, 2001, pp. 397-403, XP027361281, ISSN: 0920-5861, [retrieved on Feb. 20, 2001].

Sun M et al: "Significant effect of acidity on catalytic behaviors of Cs-substituted polyoxometalates for oxidative dehydrogenation of propane", Applied Catalysis A: General, Elsevier Science, Amsterdam, NL, vol. 349, No. 1-2, Oct. 31, 2008, pp. 212-221, XP025432574, ISSN: 0926860X, DOI: 10.1016/J.APCATA.2008.07.035 [retrieved on Aug. 3, 2008].

Furuta, M.; Sakata, K.; Misono. M.; Yoneda, Y., "Structure and Acidity of 12-Molybdophosphoric Acid and Its Salts in Solid State as Characterized by Infrared Spectroscopy", Chem. Lett. (1979) pp. 31-34.

Misono, M.; Mizuno, N.; Katamura, K.; Kasai, A.; Konishi, Y.; Sakata, K.; Okuhara, T.; Yoneda, Y., "Catalysis by Heteropoly Compounds. III. The Structure and Properties of 12-Heteropolyacids of Molybdenum and Tungsten ($H_2PMo_{12-x}W_xO_{40}$) and Their Salts Pertinent to Heterogeneous Catalysis", Bull. Chem. Soc. Jpn. vol. 55, No. 2 (1982) pp. 400-406.

Petrochemical Processes, vol. 1, 1989, by Alain Chauvel, Gilles Lefebvre. 62 pages.

Izumi. Y.; Hasebe, R.; Urabe, K., J. "Catalysis by Heterogeneous Supported Heteropoly Acid" Catal. 84 (1983) pp. 402-409.

Miao Sun, et al., "Significant Effect on Acidity on Catalytic Behaviors of Cs-Substituted Polyoxometalates for Oxidative Dehydrogenation of Propone," Applied Catalysis A: General (2008); pp. 212-221.

Yamamura, T.; Nakatomi, S., J. "Surface Acidity of Phosphotungstic Acid-Alumina Catalyst and Its Activity for Propylene-Ethylene Codimerization" Catal. 37 (1975) pp. 142-147.

Vaughan, S.; O'Connor, C. T.; Fletcher, J. C. Q., J. "High-Pressure Oligomerization of Propene over Heteropoly Acids" Catal. 147 (1994) pp. 441-454.

Chen, G.; Li, J.; Yang, X.; Wu, Y., Appl. "Surface-appropriate lipophobicity-Application in isobutene oligomerization over Teflon-modified silica-suppported 12-silicotungstic acid" Catal. A: Gen. 310 (2006) pp. 16-23.

Zhang, J.; Kanno, M.; Zhang, J.; Ohnishi, R.; Toriyabe, K.; Matsuhashi, H.; Kamiya, Y., J. Mol. "Preferential oligomerization of isobutene in a mixture of isobutene and 1-butene over sodium-modified 12-tungstosilicic acid supported on silica" Catal. A: Chem. 326 (2010) 107.

Zhang, J.; Ohnishi, R.; Okuhara, T.; Kamiya, Y., "Preferential oligomerization of isobutene in mixtures of isobutene and 1-butene over 12-tungstosilicic acid supported on silica", Appl. Catal. A: Gen. 353 (2009) 68-73.

Tatematsu, S.; Hibi, H.; Okuhara, T.; Misono, M., "Preparation Process and Catalytic Activity of $Cs_xH_{3-x}PW_{12}O_{40}$" Chem. Lett. (1984) pp. 865-868.

Okuhara, T.; Kasai, A.; Hayakawa, N.; Yoneda, Y.; Misono, M., "Catalysis by Heteropoly Compounds. VI. The Role of the Bulk Acid Sites in Catalytic Reactions over $Na_xH_3$-$xPW_{12}O_{40}$", J. Catal. 83 (1983) 121.

Okuhara, T.; Nishimura, T.; Watanabe, H.; Na, K.; and Misono, M., in "Novel Catalysis of Cesium Salt of Heteropoly Acid and its Characterization by Solid-state NMR", Studies in Surface Science and Catalysis, 90 (1993) 419-428.

Okuhara, T.; Nishimura, T.; Watanabe, H.; Misono, M., J. Mol. "Insoluble Heteropoly compounds as highly active catalysts for liquid-phase reactions" Catal. 74 (1992) pp. 247-256.

Ghosh, A. K.; Moffat, J. B., J. "Acidity of Heteropoly Compounds" Catal. 101 (1986) pp. 238-245.

Ren, Yuanhang, et al. "Progress of the Application of Mesoporous Silica-Supported Heteropolyacids in Heteroheneous Catalysis and Preparation of Nanostructured Metal Oxides" Materials. 2010, 3, pp. 764-785, doi:10.3390/ma3020764, ISSN.

* cited by examiner

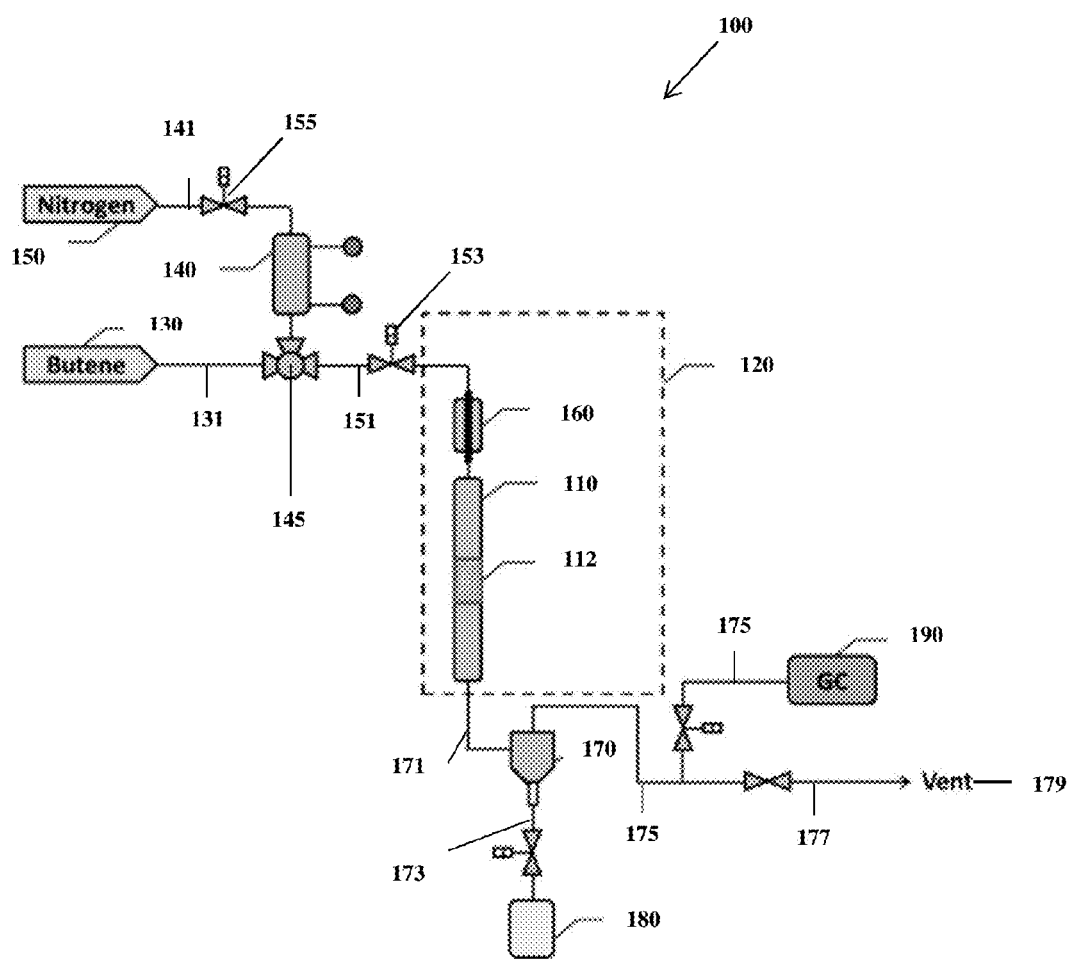

UNSUPPORTED METAL SUBSTITUTED HETEROPOLYACID CATALYSTS FOR DIMERIZATION AND/OR OLIGOMERIZATION OF OLEFINS

TECHNICAL FIELD

This invention relates to unsupported metal (e.g., cesium) substituted heteropolyacid catalyst compositions useful for the production of butene dimers and/or oligomers by dimerization and oligomerization from mixed butenes, in which, under mild conditions, all isomers of mixed butenes produce highly branched C8 and C8+ olefins which are useful as octane enhancers.

BACKGROUND

The quality of fuels with lower emissions is very important owing to more and more restrictive fuel legislations in the world. High research octane number (RON) will need to be maintained, while the aromatic content will be reduced below 35 vol % level. Aromatic compounds have the greatest contributions to RON of gasoline. Reducing the content of aromatics will cause significant reductions in the quantity of gasoline and RON deficiencies. In addition, as aromatic compounds have a lower vapor pressure, the volatility of the gasoline will increase with the reduction of aromatics. Consequently, the cost of gasoline production will increase to maintain the acceptable level of Reid Vapor Pressure (RVP) since the blending of light hydrocarbons such as $C_4$-$C_5$, which are relatively cheap, will have to be reduced. Methyl-tertiary-butyl-ether (MTBE) provides a considerable octane supply to the gasoline and contributes a significant diluting effect owing to its high blending concentrations (10-15%). For the past twenty years or so, gasoline sold in the United States and many other countries has been blended with up to 15% volumes of MTBE, an oxygenate, in order to raise the octane rating and to reduce environmentally harmful exhaust emissions. Unfortunately, MTBE is itself a pollutant, having an objectionable and strong odor and taste at extremely low concentrations (ppb) and having been classified as a potential human carcinogen. The concentration of undesired components, such as, benzene, aromatics, sulfur will be reduced when 15% volumes of MTBE is blended. If MTBE is removed without adding other diluents, this beneficial dilute effect would be lost.

One replacement for MTBE is fermented grain ethanol from wheat or sugar cane. U.S. Pat. No. 4,398,920(A) describes a blended fuel comprising a mixture of ethanol, acetone, and methanol from fermentation. Knowing the toxicology of ethanol and that ethanol provides a higher blending RON shows advantages of ethanol. However, the production of ethanol is costly and it is economically sustainable only when tax reductions are granted. Furthermore, producing sufficient quantities of grain ethanol to satisfy the needs of the transportation industry will compete with limited food supplies. Further, ethanol has relatively low energy content when compared to gasoline. Ethanol contains about 76,000 Btu's/gallon while gasoline contains about 113,000 Btu's/gal. Also, ethanol has high affinity towards water and it cannot mix together with the gasoline directly in the refinery but is only added just before the last distribution point in the network. Moreover ethanol easily forms low-boiling azeotropic mixtures with the components of gasoline which leads to higher RVP which varies from 17 to 22 psi at 10-15% blending levels. However, high vapor pressure is a problem especially in the summer months. In addition, excessively high concentrations of ethanol (about 10% of ethanol by volume) seem to cause increase in the emissions of $NO_R$.

The use of ethanol could provide various advantages such as known toxicology and higher blending RON. However, ethanol usages are limited by the costly production, relatively low energy content, high affinity towards water, on-site blending limitations and higher RVP.

Therefore for reasons brought forth above, an effective replacement for MTBE and ethanol in gasoline as an octane enhancer is needed to raise the octane ratings of gasoline and reduce deficits from their use.

Mixed butenes are often used as feeds for an alkylation process. The production of alkylates are not however an environmentally friendly process because of the mixed spent acids. In addition, alkylates have lower RON and Octane Sensitivity. Therefore an effective replacement for alkylates, MTBE and ethanol in gasoline is needed to raise the octane ratings of gasoline. The use of high-octane hydrocarbon components could enable the problems described herein above to be overcome. Further, C8 olefins as RON enhancers show many advantages over currently used octane enhancers, such as MTBE or ethanol, and alkylates.

Alkylates which include iso-octane and trimethyl pentanes are extremely desirable for their higher RON, low RVP and their positive influence on emissions. Alkylation is a refinery process which consists of the formation of highly branched paraffins by the catalytic alkylation reaction of isobutane with light olefins such as propylene and butenes in the presence of $H_2SO_4$ or HF. From an environmental point of view, both $H_2SO_4$ and HF are strong acids. The handling of enormous volumes of $H_2SO_4$ or HF in routine operations, disposals of its by-products and transporting the acid for its recovery are high risk owing to their corrosive nature. The production of alkylates is not an environmental friendly process. In addition, alkylates have Motor Octane Number (MON) comparable to their RON and hence have lower octane sensitivity. In modern and future high efficiency, spark ignition engines, fuels with higher octane sensitivities for a given RON will have better anti-knock quality and allow higher combustion efficiency.

Therefore, there is strong incentive for the use of high-octane hydrocarbon components deriving from the dimerization or oligomerization of butenes which can overcome the problems described above and show many advantages over currently used, MTBE, ethanol or alkylates as RON enhancers. The major compounds obtained from the dimerization/oligomerization of mixed butenes are C8 and C12, olefins. Among butene dimers, diisobutenes (DIBs) is the most preferred one which is a non-oxygenative fuel component with many advantages such as higher RON, higher octane sensitivity or better anti-knock quality, higher energy content compared to MTBE and alkylates, lower RVP than MTBE and ethanol. Highly branched octenes have a number of advantages including: giving very similar RON increases as MTBE when the same volume is added to a low RON gasoline; having higher RON sensitivities compared to MTBE and alkylates and hence, will have a better anti-knock quality and higher combustion efficiency in modern and future spark ignition engines and having a higher energy content compared to MTBE and lower RVP, while not increasing RVP like MTBE and ethanol. Further, at 15% blending volume to a 91 RON gasoline, DIBs will have about 2.8% more energy per liter over MTBE. Thus on average, there will be a saving of 2.8% by volume of total gasoline consumption.

There are mainly two types of light aliphatic olefin dimerization mechanisms, one is acid-catalyzed ionic mechanism and another is metal-catalyzed coordinative mechanism. The acid catalyzed processes provide strongly branched olefins while the coordinative metal complex-catalyzed processes produce largely linear olefins or mainly head-tail and head-head dimerization and oligomerizations of double bonds of the olefins. Strongly branched octenes such as dimethyl-hexene and trimethyl-pentene have high Research Octane Number (RON), so acidic catalysts are mostly welcomed for producing gasoline enhancers. On the other hand, the coordinative metal complex-catalyzed processes often use Ziegler type catalysts, nickel, cobalt, iron complexes based catalysts, titanium, and zirconium based single site catalysts. Aluminum base Lewis acid catalyst and supported nickel oxides give predominantly linear type of olefins. The coordinative metal complex-catalyzed processes have been studied extensively. Such processes, both homogeneous and heterogeneous, are normally complicated and require moisture and air free environment. The coordinative metal complex-catalyzed processes normally use 1-butene as starting material as well.

Heteropolyacids (HPAs) such as $H_3PW_{12}O_{40}$ and $H_3PMo_{12}O_{40}$ are strong Brønsted acids. According to a Hammett acidity function, the acidity of $H_3PW_{12}O_{40}$ is less than −8.2 and that will put such acids into a super-acid region.

Therefore, HPA is used as a catalyst in various reactions due to its high acidity and oxidative nature. The first industrial process using a HPA based catalyst was for the hydration of propylene to isopropanol in aqueous solutions.

Olefin dimerizations or oligomerizations are industrial important reactions to convert light olefins (C2-C5) into higher olefins often catalyzed by strong acids. The products can be used as feedstocks for other valuable petrochemicals. The Bayer process operates at 100° C. with an ionic exchange resin catalyst to give 75% of dimers and 25% of trimers with high conversion ratio from isobutene. The dimerization and oligomerization of linear butene with UOP's Octol process using phosphoric acid physically absorbed on a support or IFP's Dimersol X process based on a nickel salt/aluminum alkyls catalyst gave less branched octenes which are useful for the preparations of plasticizers. Selective dimerization of isobutene are particular interested by industry since the separation of individual butene isomers appear difficult especially for isobutene and 1-butene which almost have identical boiling points. One method to separate isobutene from mixed butenes involves the selective dimerization or oligomerization of isobutene. HPA dissolved in water has been reported as effective catalysts for such process. Traces amount of isobutene in C4 mixtures can be removed by such HPA or its salts such as $Cr^{3+}$, $La^{3+}$, $Al^{3+}$, $Fe^{3+}$, $Cu^{2+}$, $Cd^{2+}$, $Ca^{2+}$, and $Zn^{2+}$ through selective isobutene dimerizations as well. However, due to the corrosive nature of HPA, the processes using the unsupported HPA often require high maintenances. Solid acid or supported catalysts are preferred for industrial processes since such process is less hazardous and more easily to be operated. Unfortunately, when HPA or its water soluble salts is supported directly, on $SiO_2$ for example, the acid strength decreases. Therefore, a lower activity using supported HPA catalysts for olefin dimerization is expected. Such supported HPA acids have been reported in the literature and used to catalyze the light olefin dimerizations and oligomerizations since the eighties. JP 57014538A teaches selective oligomerizations of isobutene into polyisobutene from a mixtures of 1-butene and isobutene using HPA or its salt as catalyst at 70° C. Only isobutene was oligomerized with 99.3% conversion and 99.9% selectivity for the oligomer. $Al_2O_3$-supported $H_3PW_{12}O_{40}$ has been reported to be able to catalyze propylene-ethylene codimerization at 573 K to form pentenes with a selectivity of 56% (butenes 17%, hexenes 27%). Propylene oligomerization proceeded on various kinds of salts of $H_3PW_{12}O_{40}$.

The activities of the salts decrease in the order Al>Co>Ni, $NH_4$>H, Cu>Fe, Ce>K. As expected both selectivity and conversion of such supported HPA catalysts are low.

Previously, a process of oligomerizing olefins using supported HPA catalysts to produce synthetic lubricant has been reported. In addition, oligomerization of a mixed C6 and C8 olefins with HPA catalysts has been reported.

JP 2005015383 discloses an oligomerization process catalyzed by a supported HPA catalyst for selective productions of trimer of isobutene.

Teflon modified $H_4SiW_{12}O_{40}/SiO_2$ can be used to catalyze dimerizations of isobutene in fixed bed reactor with continued isobutene flow. However, the isobutene conversion was relatively low and selectivity towards C8 olefins was poor.

Silica supported water soluble HPA salts, such as Li/Na/K salts of HPA, had been disclosed by Kamiya for butene dimerization/oligomerization. However the activity and selectivity of such catalysts are poor with only 26% of dimer, 23% trimers and 4% tetramers when the total conversion of isobutene at 97%. Direct supported HPA or its salts are prone to leaching and deactivated quickly.

Performance of catalysts more sufficient for industrial processes is important. Therefore, there is a demand for development of a novel catalyst free from leaching and having higher activity.

As described herein before, there is a need to develop other means to replace MTBE and ethanol in gasoline as an octane enhancer. Also there is a need to replace MTBE, ethanol or alkylates as RON stabilizers or enhancers.

However, there are issues involving maintenance, leaching out of catalysts, lower inefficient activities of catalysts, and poor selectivity which need to be addressed.

Further, solution HPA can be used to catalyze the light olefin oligomerizations effectively. However, such catalysts are corrosive in nature and require high maintenances. In addition, supported HPA have been used in selective isobutene dimerization/oligomerization to produce isobutene dimers/trimers. Such catalysts are prone to be leached out, deactivation and having lower activities comparing to free HPA.

The present invention provides metal salts of heteropolyacid unsupported solid catalyst compositions useful for the production of butene dimers and/or oligomers through dimerization and oligomerization of mixed butenes.

SUMMARY

The present invention is directed in one aspect to a process of using an unsupported metal (e.g., cesium) substituted heteropolyacid catalyst composition for the production of butene dimers and/or oligomers from mixed butenes, in which, under mild conditions and in the presence of the catalyst, all isomers of the mixed butenes produce highly branched C8 and C8+ olefins. The mixture of C8 olefins in this invention is mixed octenes, which are dimers of mixed butenes. C8+ olefins stand for the oligomers of mixed butenes with a carbon number of 12, 16 or 20. Mixed olefins include but are not limited to 1-butene, 2-cis-butene, 2-trans-butene and isobutene.

In a particular embodiment of the invention, isobutene in a mixed butenes feed can be selectively oligomerized with single pass conversion in a fixed bed reactor as high as 99% under mild conditions of about 40° C. while the selectivity of C8 and C12 olefins was greater than 95% in the presence of the unsupported cesium substituted heteropolyacid catalyst.

Particular embodiments of the invention further include that the catalyst compositions of the present invention are non-corrosive, produce highly branched C8 and C8+ olefins, are highly selective to C8 olefins, have high single pass conversion in a fixed bed reactor and high selectivity of isobutene under mild temperature conditions and complete butene oligomerization with all the isomers of butane under higher temperature conditions.

The unsupported water insoluble cesium substituted HPA catalysts of the invention have high selectivity towards dimerization/oligomerization of isobutene from mixed butenes under mild conditions and with high stability.

In accordance with one embodiment, the catalyst is represented by Formula (I):

$$Z_xH_yDM_{12}O_{40} \quad (I)$$

wherein:
D is B, Si, P, Ge or As;
M is Ti, V, Cr, Mn, Fe, Co, Ni, Cu, Zn, Ga, Zr, Nb, Mo, or W;
Z is Cs, Nb, Pt, Au, Pd, Rh, Ag, Cu, Fe or Ni;
x is 0<x<5; and
y is 0<y<5.

One preferred catalyst compound of the invention is an unsupported cesium substituted heteropolyacid compound having the molecular formula: $Cs_{2.2}H_{0.8}PMo_{12}O_{40}$.

In particular, it is an object of the invention to provide a novel catalyst composition of unsupported cesium substituted heteropolyacid of molecular formula $Cs_{2.2}H_{0.8}PMo_{12}O_{40}$ in a process for dimerization/oligomerization of isobutene selectively from mixed butenes in a fixed bed reactor under conditions of about 40° C. to about 300° C. and a pressure of about 1 to about 80 bar over a time period of about 30 minutes to about 1000 minutes and/or dimerization/oligomerization of all isomers of mixed butenes under temperature conditions above 80C.

In particular, it is yet another object of the invention to provide a process for converting mixed butenes to highly branched C8 and C8+ olefins using a single pass fixed bed process in the presence of a solid unsupported cesium substituted heteropolyacid catalyst composition.

BRIEF DESCRIPTION OF THE DRAWINGS

A more complete appreciation of the invention and many of the advantages thereof will be readily understood by reference to the following detailed description when considered in connection with the accompanied drawing wherein:

FIG. 1 shows a system including a fixed bed process reactor that contains the catalyst of the present invention for olefin dimerization and/or olefin oligomerization.

DESCRIPTION OF THE PREFERRED EMBODIMENTS

The present invention overcomes the deficiencies and limitations of the prior art and is directed, in one aspect, to a process for the dimerization and oligomerization of mixed olefins (in particular mixed butenes) using an unsupported metal (e.g., cesium) substituted heteropolyacid catalyst to produce highly branched C8 and C8+ olefins. More specifically and according to one embodiment, the present invention is a single stage (single pass) process that is performed under mild conditions resulting in high conversion rates as discussed below. The catalyst described herein can thus be used for dimerization/oligomerization of isobutene selectively from mixed butenes under mild conditions and/or for the dimerization/oligomerization of all isomers of mixed butenes under higher reaction temperature.

The unsupported metal (e.g., cesium) substituted heteropolyacid catalysts (either Brønsted or Lewis acid in nature) together with the mild reaction conditions of the reactor prevents cracking products and catalyst deactivation which are often encountered by using zeolite based catalysts that are used in other commercial processes. The catalyst compositions described herein allow for highly branched butene dimers/oligomers to be selectively produced from relatively low value mixed butenes. The mixed butene dimers/oligomers products consist of C8, C12 and C12+ olefins, which, as described herein, can be used octane enhancing compositions and/or as a re-cracking feed stream. In certain embodiments described herein, the reactor based system that includes the catalysts of the present invention results in the isobutene in the mixed butenes feed stream to be selectively oligomerized with a single pass conversion as high as 99% under mild conditions (e.g., about 40° C. in certain embodiments), while the selectively towards the production of highly branched C8 olefins and C12 olefins is over 95%.

As described herein, the product stream can be combined with a fuel component to produce the fuel composition.

Mixed Olefins (Butenes)

Mixed butenes have four structural isomers, 1-butene, 2-cis-butene, 2-trans-butene, and isobutene. Optionally, other low olefins, such as propylene and ethylene, can also be present in the feed as described below. In addition, the term "higher olefins" refers to olefins that are formed as a product as part of the present process and have a greater carbon number than the olefins in the initial feedstock introduced into the reactor.

Diisobutenes (DIBs) or Isooctenes

Diisobutenes include two isomers of 2,4,4-trimethyl-1-pentene and 2,4,4-trimethyl-2-pentene.

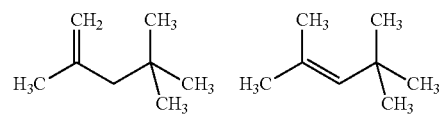

Oligomerization

Oligomerization of mixed butenes includes oligomerization of all butene isomers including the oligomerization (dimerization) of isobutene, as well as the other isomers of butene.

Dimerization of Isobutene

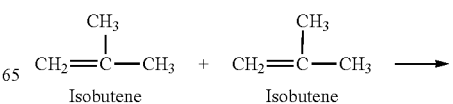

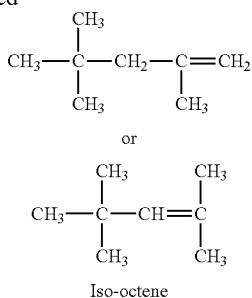

Iso-octene

C8 Olefins:

The mixture of C8 olefins mentioned in the present invention is mixed octenes, which are dimers of mixed butenes. There are a total 72 isomers of the octenes and only a few of them have high RON values. There are two types of olefins, namely branched and linear (straight chained). Highly branched octenes are very important RON enhancers for gasoline and thus, the production of these types of octenes is desirable. Some of the C8 olefins are highly branched such as dimethyl-hexene and trimethyl-pentene. C8 olefins may also be linear or with fewer branches which are not the subject of this invention. It will also be appreciated that cyclic products can also be formed by this process.

C12 and C12+ Olefins:

C12 olefins stand for the oligomers of mixed butenes with a carbon number of 12 and C12+ olefins stand for the oligomers of mixed butenes with a carbon number of 16 or 20. The cyclic products can also be formed by this process.

The Present Dimerization/Oligomerization Process

As described herein, effective processes for the dimerization/oligomerization of isobutene selectively from a mixed butenes feed and/or dimerization/oligomerization of all isomers of mixed butenes are provided as embodiments of the present invention. In particular, processes for producing highly branched C8 and C8+ olefins from mixed olefins are provided as embodiments of the present invention and more particularly, highly branched olefins, including C8, C12, and C12+ olefins, are formed. Additionally, processes for producing fuel compositions that include oligomers prepared from mixed butenes and/or other olefins are also provided as embodiments of the present invention.

For example, in one embodiment of the present invention, a mixed olefin feedstock is contacted with a catalyst at the appropriate reaction conditions (oligomerization conditions) and preferably as part of a single stage process (single pass) to produce a product stream that includes oligomers. More specifically, a mixed butenes feedstock is contacted with a catalyst at the appropriate reaction conditions to produce a product stream that includes highly branched C8 and C8+ olefins, including DIBs. The product stream can be combined with a fuel component to produce the fuel composition. The fuel component of the fuel composition can be selected from gasoline, diesel, jet fuel, aviation gasoline, heating oil, bunker oil, or a combination thereof, or other suitable fuel components within the spirit of the present invention. In certain embodiments including preferred embodiments, the resultant fuel composition has an increased RON and reduced RVP, without the presence of other chemicals that can have deleterious effects on the environment.

The source of the mixed olefin stream can vary and can encompass any number of different sources of feedstocks (feed streams) that are suitable for use in the present invention. For example, in some embodiments of the present invention, the mixed olefin stream can be a discharge stream from an FCC unit or thermal cracking unit, a raffinates stream from an MTBE process, a raffinates stream from TBA process, liquid petroleum gas (LPG) stream or a combination thereof. It will further be understood that other sources of the mixed olefin stream are within the scope of the present invention. In accordance with the disclosed embodiments, the mixed olefin stream can include a mixed butenes stream. In another embodiment, the mixed olefin stream can be in the form of a mixed C3 to C5 olefins feed stream. In yet other embodiments, the mixed olefin stream can include one or more of polypropylene, n-butylene, 2-butene, isobutylene, pentenes, hexenes, olefins having more than six carbons, etc. Other suitable sources for the mixed olefin stream and types of olefins will be apparent to those of skill in the art and are to be considered within the scope of the present invention.

In accordance with one preferred embodiment of the present invention, the mixed butenes feed (stream/feedstock) used in this invention is a liquid mixture of at least two and preferably all four of the isomers of 1-butene, isobutene, 2-trans-butene and 2-cis-butene. These relatively low value mixed butene feeds can come directly from refinery tail gases.

Different butene isomers have different activities toward dimerization or oligomerization. For example, isobutene is predisposed to being dimerized or oligomerized. In contrast, it is generally very difficult for 2-butenes, especially 2-trans-butenes, to form the correspondent dimers or oligomers. One type of process focuses on the selective dimerization of one butene isomer in that the process is specifically tailored to dimerizing one isomer of butene. This process limitation thus results in a product stream being formed that is of predominantly one olefin type. The present catalyst compositions work in such a scheme.

Alternatively and also in accordance the present invention, the present process and catalyst compositions allow all four isomers of butene to be effectively dimerized or oligomerized under relatively mild conditions with high single pass conversion rates and high selectivity towards C8 olefins (along with production of C12 olefins and smaller amounts of C12+ olefins).

In one embodiment, the mixed butenes feed consists of all four butene isomers in varying quantities as will be appreciated by a review of the Examples presented herein. However, as previously mentioned and in accordance with another embodiment of the present invention, the feed can include at least two butene isomers, as well as other C3-C5 olefins, such as propylene and ethylene.

FIG. 1 illustrates one exemplary system 100 for performing dimerization/oligomerization of mixed butenes in accordance with the present invention. FIG. 1 likewise shows an exemplary process flow. FIG. 1 shows the implementation of the present invention in a fixed bed process. The system 100 includes a reactor 110 which can be in the form of a fixed bed reactor vessel. A catalyst, of the type disclosed herein, is loaded within a zone or region 112 that is within the reactor 110 as shown. In the illustrated embodiment, the catalyst is centrally located within the reactor 110. The reactor 110 is disposed within a hotbox which is generally shown at 120.

The reactants are delivered to the reactor 110 in the following manner. A source of feedstock (e.g., the mixed butenes feed) is identified at 130 and the source 130 is fluidly connected (e.g., by means of a fluid conduit 131

(such as a pipe)) to a storage receptacle 140 to allow the feedstock to be stored in the storage receptacle 140. As mentioned herein, the feedstock is typically a liquid stream.

A valve or flow control device 145 is disposed along the conduit to control the flow of the feedstock to both the storage receptacle 140 and the reactor 10. In addition, a means 150 for delivering the feedstock (mixed butenes) into the reactor 110 at a desired rate is provided. The means 150 is in communication with the storage receptacle 140 via a conduit 141 and is configured to operatively cause the feedstock to be delivered at a desired flow rate to the reactor 110. In one embodiment, the means 150 is in the form of a gas source (such as $N_2$) that is used to press the liquid feedstock into the reactor 110 at a desired rate (flow rate). The gas source 150 is connected to the storage receptacle 140 by means of a conduit (e.g., pipe) that can include a valve or the like 155 for controlling the flow of the gas to the storage receptacle 140.

The valve 145 can be placed into a position that closes off the flow from the source 130 to the storage receptacle 140; however, the combined gas (from source 150) and the stored feedstock within the storage receptacle 140 are permitted to flow through the valve 145 toward the reactor 110. A conduit 151 can lead from valve 145 to an inlet of the reactor 110. Within the conduit 151, there can be a valve 153 that controls the flow the feedstock to the inlet of the reactor 110.

Before entering an inlet of the reactor 110, the feedstock passes through a heat exchange device 160 that is located between valve 145 and the reactor 110. The heat exchange device 160 is configured to adjust the temperature of the feedstock to a preselected temperature (e.g., a selected reactor temperature) prior to the feedstock entering the reactor 110. After passing through the reactor 110 and into contact with the catalyst in region 112, olefin products are formed as discussed herein and these products exit an outlet of the reactor 110 via a conduit 171 and are introduced to a separator 170. As described herein, the reactor 110 can be a single stage reactor in which the feedstock flows once therethrough and into contact with the catalyst to form the product stream. The conversion rates can thus be described as being single pass conversion rates.

The separator 170 can be in the form of a liquid/gas separator in which the olefin products with high boiling points are cooled down and flow through a conduit 173 before being collected as a liquid sample which is generally indicated at 180. Unreacted feedstock is removed from the separator 170 via a different outlet for further processing and/or recycle. For example, the unreacted feedstock (e.g., unreacted butenes) can flow through a conduit 175 be analyzed by an online gas chromatograph 190 or can simply be vented through a conduit/line 177 that leads to a vent 179. One or more valves can be included in the line 177 as shown.

It will be appreciated that the products (liquid sample 180) can be then further processed and/or transported to another location.

The reaction parameters vary depending upon a number of factors, including the type of feedstock, the catalyst composition, etc. In one embodiment, the reactor 110 operates at a temperature of about 40° C. to about 300° C. and at a pressure of about 1 to about 80 bar over a time period of about 30 minutes to about 1000 minutes.

Exemplary Catalysts

As mentioned herein and in accordance with one embodiment, the fixed bed reactor 110 has at least one region 112 that is loaded with a catalyst which is suitable for use in the particular present invention. Exemplary catalysts include a class of metal (e.g., cesium) substituted heteropolyacid (HPA) catalysts (preferably in unsupported form) which can effectively dimerize/oligomerize mixed butenes as discussed herein. As discussed, under mild reaction conditions which are described herein, this type of catalyst will prevent cracking products and leads to the production of more highly branched C8 and C8+ olefins with milder reaction conditions compared with other classes of catalysts such as, nickel oxide and zeolite-based catalysts.

Particular embodiments of the invention further include that the cesium salts of heteropolyacid are non-corrosive, produce highly branched C8 and C8+ olefins, are highly selective to C8 olefins, have high single pass conversion in a fixed bed reactor and high selectivity of isobutene under mild temperature conditions and complete butene oligomerization with all the isomers of butene.

The unsupported water insoluble cesium substituted HPA catalysts of the invention have high selectivity towards dimerization/oligomerization of isobutene from a mixed butenes feed under mild conditions and with high stability.

In accordance with the present invention there is provided unsupported cesium substituted heteropolyacid catalyst compounds represented by Formula (I):

$$Z_xH_yDM_{12}O_{40} \qquad (I)$$

wherein:
D is B, Si, P, Ge or As;
M is Ti, V, Cr, Mn, Fe, Co, Ni, Cu, Zn, Ga, Zr, Nb, Mo, or W;
Z is Cs, Nb, Pt, Au, Pd, Rh, Ag, Cu, Fe or Ni;
x is 0<x<5; and
y is 0<y<5;
wherein B is Boron, Si is Silicon, P is Phosphorus, Ge is Germanium, As is Arsenic, Ti is Titanium, V is Vanadium, Cr is Chromium, Mn is Manganese, Fe is Iron, Co is Cobalt, Ni is Nickel, Cu is Copper, Zn is Zinc, Ga is Gallium, Zr is Zirconium, Cs is Cesium and W is Tungsten.

Thus, cesium (Cs) can be substituted with another metal Z such as Nb, Pt, Au, Pd, Rh, Ag, Cu, Fe or Ni, wherein Nb is Niobium, Pt is Platinum, Au is Gold, Pd is Palladium, Rh is Rhodium, Ag is Silver, Cu is Copper, Fe is Iron and Ni is Nickel.

Among the broadly preferred groups of compounds of Formula (I) of this invention are those in the subgroups below wherein the other variables of Formula (I) in the subgroups are as defined above wherein: D is B, Si, Ge or P; M is Ti, V, Mo, Ni or W; x is 0<x<5; and y is 0<y<5.

Among the additionally preferred groups of compounds of Formula (I) of this invention are those in the subgroups below wherein the other variables of Formula (I) in the subgroups are as defined above wherein: D is B, Si, or P; M is Ti, V, Mo or W; x is 0<x<5; and y is 0<y<5.

Among the additionally preferred groups of compounds of Formula (I) of this invention are those in the subgroups a, b, c and d below wherein the other variables of Formula (I) in the subgroups are as defined above wherein: (a) D is P and M is Mo; (b) D is P and M is W; (c) D is Si and M is Mo; and (d) D is Si and M is W.

Preferred compounds of the invention are cesium substituted heteropolyacid catalysts having the molecular formula: $Cs_{2.2}H_{0.8}PMo_{12}O_{40}$. In one embodiment, the reactor 110 is charged with the calcinated, dried and sieved $Cs_{2.2}H_{0.8}PMo_{12}O_{40}$ catalyst of Example 1 (described below).

The unsupported cesium substituted HPA catalysts of the invention have both Brønsted and Lewis acidities and together with mild reaction conditions as low as 40° C. will prevent cracking products and catalyst deactivation which are often encountered by using zeolite based catalysts in other commercial processes.

The compounds of this invention may be prepared from (a) commercially available starting materials (b) known starting materials which may be prepared as described in literature procedures or (c) new intermediates described in the schemes and experimental procedures herein. In addition, the catalyst compounds of the present invention can be prepared using any number of conventional processes that are suitable in view of the teachings of the present invention including, but not limited to, the process described in Miao Sun, et al., "*Significant Effect on Acidity on Catalytic Behaviors of Cs-Substituted Polyoxometalates for Oxidative Dehydrogenation of Propone*," Applied Catalysis A: General (2008); pp. 212-221, which is hereby incorporated by reference in its entirety.

Standard Catalyst Testing Procedures

Evaluation of representative catalysts of this invention in Standard Test Procedures indicates that the compounds of the invention possess significant catalyst activity for the preparation of highly branched C8 and C8+ olefins under mild conditions. The branched butene dimers/oligomers products have relatively higher octane and lower Reid Vapor Pressure (RVP) than alkylation products that could be used as fuel constituents to boost the required octane value of fuel.

The products of the present invention are in the form of a stream that includes mainly C8 olefins and C12 olefins, with a small amount of C16 olefins, C16+ olefins, and cyclic compounds. Among the C8 olefins produced, the preferred one is DIB since as described herein, DIB has advantageous properties in terms of acting as an octane enhancer. The reaction in the present invention has high selectivity for C8 olefins—including DIB—as well as C12 olefins. In one embodiment, the present invention utilizes relatively low value mixed butene feeds to produce DIB and other valuable, highly-branched C8 and C8+ olefins. In other words, the mixed butene feeds for use in the present process produce not only DIB but other desirable olefins (e.g., highly branched higher olefins) as a result of operation conditions and process steps described herein. However, in an alternative embodiment, selective oligomerization of isobutene from the mixed butenes stream can occur using the catalysts described herein.

The products of the present invention, namely highly branched C8 and C8+ olefins with high RON values, are extremely valuable in the fuel industry. With the increasingly restrictive regulations on gasoline as mentioned above, highly branched C8 and C8+ olefins provide an alternative non-oxygenated octane enhancer that meets those restrictions. Specifically, highly branched C8 and C8+ olefins can increase RON and lower RVP in fuel without the negative environment impact seen with MTBE or aromatics. The process of the present invention thus achieves this objective by producing a product that includes not only highly branched C8 olefins but also produces other highly branched olefins that have a carbon number more than 8.

The C8 and C8+ olefins produced through the present invention can also be used as valuable feedstock. Specifically, the C8 and C8+ olefin products can be utilized as premium feeds for Fluid Catalytic Cracking (FCC) processes such as Deep Catalytic Cracking (DCC) and High Severity Fluid Catalytic Cracking (HSFCC) processes to produce highly demanded light olefins such as ethylene and propylene. A mixture of dimers and trimers which have a large number of allylic hydrogens are considerably more reactive and have proven to be the most desirable feeds for FCC based cracking processes such as HSFCC and DCC. These C8 and C8+ products may also be used as intermediates in synthesizing detergent, plasticizer, pesticide, lubricants, additives, flavors, medicine and many other fine industrial chemicals.

EXAMPLES

The invention will be more fully described in conjunction with the following specific examples which are not to be construed as limiting the scope of the invention.

The following experiments were conducted at a pilot plant having the configuration and characteristics of the system 100 illustrated in FIG. 1.

The mixed butenes feed stream was used without any purification and the composition of the mixed butenes feed can be: 1-butene (about 21%); isobutene (about 35%); 2-cis-butene (about 19%); and 2-trans-butene (about 25%). All percentages mentioned herein are based on weight unless otherwise noted.

Example 1

Synthesis of the $Cs_{2.2}H_{0.8}PMo_{12}O_{40}$ Catalyst

An amount of solid $Cs_{2.2}H_{0.8}PMo_{12}O_{40}$ catalyst was prepared in accordance with the method (process) described in *Applied Catalysis A: General* (2008); pp. 212-221.

Dimerization/Oligomerization

Using the reactor 110 illustrated in system 100, the calcinated, dried and sieved $Cs_{2.2}H_{0.8}PMo_{12}O_{40}$ catalyst of Example 1 was heated to the desired reaction temperature while introducing mixed butenes of feed stock test reagent to pressurize the reactor 110. The products were collected after the pressure reached 20 bar and the flow was stabilized. The tail gas samples were analyzed by online gas chromatography (GC) using a Flame Ionization Detector (FID) with Plot Q column and lines were trace heated to 105° C. to prevent any condensations. Liquid products were separated by the liquid/gas separator and collected. Total 15 mL of catalyst was loaded in this pilot test (however, it will be appreciated that the amount used depends on the scale of the reactor).

The below Table 1 further sets forth the operating reactor conditions as well as the results of Example 1.

TABLE 1

Reaction conditions
Temperature: 40° C.; pressure: 20 bar;
LHSV: 0.63 $hr^{-1}$; test period: 405 min

| Feed (percentage) | Conversion (%) | Average Conv. (%) | Products | Selectivity (%) |
|---|---|---|---|---|
| 2-trans-butene (25.2%) | 8.43 | 43.7% | C8 olefins | 65.1 |
| 1-butene (21.5%) | 4.88 | | C12 olefins | 29.8 |
| iso-butene (32.4%) | 99.05 | | C16 olefins | 4.5 |
| 2-cis-butene (20.7%) | 0.33 | | C20 olefins | 0.5 |

Legend: Liquid Hourly Space Velocity (LHSV)

Example 2

The catalyst preparation procedure of this example was the same as in Example 1.

The reaction process of this example was similar to that described in Example 1, except reaction temperature. The detailed reaction conditions are listed below in Table 2.

TABLE 2

Reaction conditions
Temperature: 170° C.; pressure: 20 bar;
LHSV: 0.63 hr$^{-1}$; test period: 1000 min

| Feed (percentage) | Conversion (%) | Average Conv. (%) | Products | Selectivity (%) |
|---|---|---|---|---|
| 2-trans-butene (25%) | 46.24 | 67.3% | C8 olefins | 52.9 |
| 1-butene (21%) | 89.55 | | C12 olefins | 33.8 |
| iso-butene (35%) | 99.71 | | C16 olefins | 10.9 |
| 2-cis-butene (19%) | 57.10 | | C20 olefins | 2.4 |

It will therefore, be appreciated that the present invention describes a process (single pass conversion) in which the mixed butenes undergo dimerization/oligomerization to produce highly branched higher olefins using unsupported cesium substituted heteropolyacid catalysts. The catalyst compositions described herein can be used for both: (a) the dimerization/oligomerization of all of the isomers of the mixed butenes or (b) the dimerization/oligomerization of isobutene selectively from the mixed butenes.

The process and the system of the present invention provide a number of advantages over the conventional dimerization/oligomerization processes. These advantages include but are not limited to: (1) providing an alternative non-oxygenated octane enhancer, highly branched C8 and C8+ olefins, to meet the increasingly restrictive regulations and reduction of aromatics in the gasoline; (2) to valorize the relatively low mixed butenes; and (3) to increase the yields of valuable light olefins of ethylene and propylene by recycle of low value butenes to premium cracking feeds (C8-C16 olefins).

It will be understood that the various chemical elements forming the catalyst compounds described herein are identified in the following claims based on the nomenclature of the period table.

While the present invention has been described above using specific embodiments, there are many variations and modifications that will be apparent to those having ordinary skill in the art. As such, the described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A process for dimerizing and oligomerizing a hydrocarbon feed comprising mixed olefins to produce mixed branched higher olefins, said process comprising the steps of:
   introducing the hydrocarbon feed into a reactor vessel under oligomerization conditions;
   contacting the mixed hydrocarbon feed with a catalyst within the reactor vessel to convert the mixed branched olefins into the mixed branched higher olefins, wherein the catalyst consists of an unsupported metal substituted heteropolyacid catalyst represented by Formula (I):

$Cs_xH_yPMo_{12}O_{40}$ (I)

wherein, x and y represent numbers; and
   producing a product stream comprising the mixed branched higher olefins from the reactor vessel;
   wherein the hydrocarbon feed comprises at least two butene isomers and the mixed branched higher olefins comprise olefins having more than 4 carbons.

2. The process of claim 1, wherein the mixed olefins consist essentially of butene isomers.

3. The process of claim 1, wherein the hydrocarbon feed comprises isobutene, and wherein the oligomerization conditions and the unsupported metal substituted heteropolyacid catalyst are selected such that isobutene is oligomerized to form diisobutene as the product stream.

4. The process of claim 1, wherein 0<x<5 and 0<y<5.

5. The process of claim 1, wherein 3>x>2 and 0<y<1.

6. The process of claim 1, wherein the mixed branched higher olefins of the product stream comprise at least about 50% by weight olefins having 8 carbons.

7. The process of claim 1, where the reactor vessel is maintained at a temperature of between about 40-300° C.

8. A process for producing a fuel composition from mixed butene isomers using a butene dimerization/oligomerization system, the process comprising the steps of:
   introducing a feed stream comprising the mixed butene isomers into a reactor vessel under oligomerization conditions;
   contacting the feed stream comprising the mixed butene isomers with a catalyst within the reactor vessel to convert the mixed butenes into mixed higher olefins that comprise olefins having at least 8 carbons, wherein the catalyst consists of an unsupported metal substituted heteropolyacid catalyst represented by Formula (I):

$Cs_xH_yPMo_{12}O_{40}$ (I)

wherein, x and y represent numbers; and
   producing a product stream comprising the mixed higher olefins from the reactor vessel; and
   combining the product stream with a fuel component to produce the fuel composition;
   wherein the fuel component comprises gasoline, diesel, jet fuel, aviation gasoline, heating oil, bunker oil, or a combination thereof.

9. The process of claim 8, wherein at least 70% by weight of the mixed butene isomers are converted into the mixed higher olefins as a result of a single pass through the reactor vessel.

10. The process of claim 8, wherein the feed stream is a discharge stream from an FCC unit, a thermal cracking unit, a raffinates stream from an MTBE process, a raffinates stream from a TBA process, a liquefied petroleum gas (LPG) stream, or a combination thereof.

11. The process of claim 8, wherein the feed stream comprising the mixed butene isomers comprises at least two butene isomers.

12. The process of claim 8, wherein the feed stream comprises isobutene, and wherein the oligomerization conditions and the unsupported metal substituted heteropolyacid catalyst are selected such that isobutene is oligomerized to at least form diisobutene as the product stream.

13. The process of claim 8, wherein 0<x<5 and 0<y<5.

14. The process of claim 8, wherein 3>x>2 and 0<y<1.

15. The process of claim 1, wherein the hydrocarbon feed comprises all butene isomers.

16. The process of claim 15, wherein the oligomerization conditions and the unsupported metal substituted heteropolyacid catalyst are selected such that all butene isomers are oligomerized to form the product stream, wherein the product stream comprises olefins having 8 carbons and olefins having more than 8 carbons.

17. The process of claim 15, wherein a weight percentage of the hydrocarbon feed of isobutene>2-trans-butene>1-butene>2-cis-butene.

18. The process of claim 15, wherein a single pass conversion of isobutene>1-butene>2-cis-butene>2-trans-butene.

19. The process of claim 8, wherein the feed stream comprising the mixed butene isomers comprises all butene isomers.

20. The process of claim 19, wherein the oligomerization conditions and the unsupported metal substituted heteropolyacid catalyst are selected such that all butene isomers are oligomerized to form the product stream, wherein the product stream comprises olefins having 8 carbons and olefins having more than 8 carbons.

* * * * *